(12) United States Patent
Escaich Ferrer et al.

(10) Patent No.: US 9,161,979 B2
(45) Date of Patent: Oct. 20, 2015

(54) IMMUNOSTIMULANT COMPOSITIONS COMPRISING A NUCLEOBASE AND A POLYSACCHARIDE OBTAINABLE FROM FUNGI, YEAST OR BACTERIA

(75) Inventors: Josep Escaich Ferrer, Barcelona (ES); Daniel Martinez Puig, Roda de Ter (ES); Carles Chetrit Russi, Banyoles (ES); Elisabet Borda Casas, Cardedeu (ES); Ken-ichi Kosuna, Sappporo (JP)

(73) Assignee: Bioiberica, S.A., Barcelona (ES)

( * ) Notice: Subject to any disclaimer, the term of this patent is extended or adjusted under 35 U.S.C. 154(b) by 175 days.

(21) Appl. No.: 13/121,147

(22) PCT Filed: Sep. 8, 2009

(86) PCT No.: PCT/EP2009/061620
§ 371 (c)(1),
(2), (4) Date: Mar. 25, 2011

(87) PCT Pub. No.: WO2010/034615
PCT Pub. Date: Apr. 1, 2010

(65) Prior Publication Data
US 2011/0213020 A1 Sep. 1, 2011

(30) Foreign Application Priority Data
Sep. 26, 2008 (ES) .................................. 200802731

(51) Int. Cl.
| | | |
|---|---|---|
| *A61K 36/07* | (2006.01) | |
| *A61K 31/716* | (2006.01) | |
| *A61K 45/06* | (2006.01) | |
| *A61K 31/198* | (2006.01) | |
| *A61K 31/7052* | (2006.01) | |
| *A61K 31/7105* | (2006.01) | |
| *A61K 31/711* | (2006.01) | |
| *A61K 36/06* | (2006.01) | |

(52) U.S. Cl.
CPC ................ *A61K 45/06* (2013.01); *A61K 31/198* (2013.01); *A61K 31/7052* (2013.01); *A61K 31/711* (2013.01); *A61K 31/7105* (2013.01); *A61K 31/716* (2013.01); *A61K 36/06* (2013.01)

(58) Field of Classification Search
CPC ............ A61K 31/198; A61K 31/7052; A61K 31/7105; A61K 31/711; A61K 31/716; A61K 45/06; A61K 36/06; A61K 2300/00
See application file for complete search history.

(56) References Cited

U.S. PATENT DOCUMENTS

| | | | |
|---|---|---|---|
| 5,231,085 A | 7/1993 | Alexander et al. | |
| 5,756,318 A * | 5/1998 | Kosuna | 435/101 |
| 6,831,067 B2 | 12/2004 | Fujii et al. | |
| 7,169,762 B2 | 1/2007 | Fujii et al. | |
| 2005/0058671 A1* | 3/2005 | Bedding et al. | 424/400 |

FOREIGN PATENT DOCUMENTS

| | | |
|---|---|---|
| EP | 0367724 A1 | 5/1990 |
| EP | 0733647 A2 | 9/1996 |
| WO | 2007/095313 A2 | 8/2007 |
| WO | WO 2007/095313 * | 8/2007 |

OTHER PUBLICATIONS

R.J. Beale et al., Crit Care Med., 27, 799-805 (1999).*
Martinez-Puig, et al.,"Dietary Nucleotide Supplementation Reduces Occurrence of Diarrhoea in Early Weaned Pigs", Livestock Science, May 2007, pp. 276-279, vol. 108, No. 1-3, XP-002568718.
Egilius L. H. Spierings, et al., "A Phase I Study of the Safety of the Nutritional Supplement, Active Hexose Correlated Compound, AHCC, in Healthy Volunteers", Journal of Nutritional Science and Vitaminology, Dec. 2007, pp. 536-539, vol. 53, No. 6, XP-002568719.
International Search Report dated of May 3, 2010.
Dalia Akramienė et al., "Effects of β-glucans on the immune system", Medicina (Kaunas), 2007, 43(8): 597-606.
Øystein Angen et al., "Respiratory disease in calves: Microbiological investigations on trans-tracheally aspirated bronchoalveolar fluid and acute phase protein response", Veterinary Microbiology, 2009, 137: 165-171.
T. Autio et al., "Etiology of respiratory disease in non-vaccinated, non-medicated calves in rearing herds", Veterinary Microbiology, 2007, 119: 256-265.
H.J. van der Fels-Klerx et al., "An economic model to calculate farm-specific losses due to bovine respiratory disease in dairy heifers", Preventive Veterinary Medicine, 2001, 51: 75-94.
A. Gil, "Modulation of the immune response mediated by dietary nucleotides", European Journal of Clinical Nutrition, 2002, 56(Suppl. 3): S1-S4.
José Maldonado et al., "The influence of dietary nucleotides on humoral and cell immunity in the neonate and lactating infant", Early Human Development, 2001, 65 (Suppl.): S69-S74.
Alan G. Mathew et al., "Antibiotic Resistance in Bacteria Associated with Food Animals: A United States Perspective of Livestock Production", Foodborne Pathogens and Disease, 2007, 4(2): 115-133.

(Continued)

*Primary Examiner* — Doug Schultz
(74) *Attorney, Agent, or Firm* — Sughrue Mion, PLLC (57) ABSTRACT

The present invention relates to compositions comprising nucleobases and/or sources of nucleobases and polysaccharides from extracts of fungi, yeasts or bacteria. Preferably, the compositions include Nucleoforce® or Nucleoforce® Dogs and AHCC®. Said compositions are useful in the treatment and prevention of immunosuppression, of the toxicity derived from chemotherapy or radiotherapy treatment, of diseases of the immune system, of cancer or an infection; and are also useful to stimulate the immune function in a mammal, including a human.

10 Claims, 6 Drawing Sheets

(56) References Cited

OTHER PUBLICATIONS

HJ Postema et al., "A study in veal calves for a possible correlation between serum immunoglobulin levels, nutrition levels and risk of disease in the first few weeks of the fattening period", Tijdschr Diergeneeskd, 1987, 112(11): 665-671.

* cited by examiner

C = Control (placebo product)
A = Nucleoforce® Dogs
B = AHCC®
A+B = Nucleoforce® Dogs + AHCC®

FIGURE 1

C = Control (placebo product)
A = Nucleoforce® Dogs
B = AHCC®
A+B = Nucleoforce® Dogs + AHCC®

FIGURE 2

C = Control (placebo product)
A = Nucleoforce® Dogs
B = AHCC®
A+B = Nucleoforce® Dogs + AHCC®

FIGURE 3

C = Control (placebo product)
A = Nucleoforce® Dogs
B = AHCC®
A+B = Nucleoforce® Dogs + AHCC®

FIGURE 4

C = Control (placebo product)
A = Nucleoforce® Dogs
B = AHCC®
A+B = Nucleoforce® Dogs + AHCC®

IMMUNOSTIMULANT COMPOSITIONS COMPRISING A NUCLEOBASE AND A POLYSACCHARIDE OBTAINABLE FROM FUNGI, YEAST OR BACTERIA

TECHNICAL FIELD OF THE INVENTION

The present invention relates to new compositions, more specifically to new immunostimulant compositions. The present invention also relates to the process for preparing the compositions, as well as to the use thereof.

BACKGROUND OF THE INVENTION

It is a known fact that nutritional interventions (enteral or parenteral nutritional support) in critical patients enable the reversion of catabolic conditions and anabolism stimulation, leading to improved recovery and survival rate.

A patient in a critical condition is one who, for example, is subjected to chemotherapy, who suffers generalised septicaemia, viral infection, surgery, burns, trauma, cancer, immunosuppressive treatment, malnutrition or generally any who require long periods of hospitalisation. All these clinical situations have a negative effect on the capacity of the immune response, increasing the risk of opportunistic infections, post-surgical complications and certain associated toxicities, for example, those resulting from chemotherapy or radiotherapy, delaying recovery and reducing the chance of survival.

The immune response is not only compromised in critical patients but also in humans and animals under stress, especially at early ages. In these cases the risk of oportunistic infections increases, especially those related to the respiratory and digestive systems. A clear example of the infections related to stress at early ages comes from animal production. In animals reared under commercial conditions these infections are especially relevant. For example, in calves, the first peak of respiratory diseases often emerges at four weeks of age, causing substantial economic losses due to medication and growth depression (H. J. Postema et al., *Tijdschr Diergeneeskd.* 1, 112(11), 665-671 (1987); H. J. van der Fels-Klerx et al., *Preventive Veterinary Medicine* 51(1-2), 75-94 (2001); O. Angen et al., *Veterinary Microbiology* 137(1-2), 28, 165-171 (2009); T. Autio et al., *Veterinary Microbiology* 119(2-4), 31, 256-265 (2007)).

In addition there is an increasing concern about the overuse of antimicrobials to threat opportunistic infections due to the appearance of antimicrobial resistance (A. G. Mathew et al., *Foodborne Pathog. Dis.* 4(2), 115-133 (2007)).

Nucleotides are low-weight intercellular compounds that play a role in almost all biochemical processes. They occur naturally in foodstuffs, although in limited quantities (<400 mg/100 g). Tissues with high rates of cellular proliferation, such as those of the immune and gastrointestinal systems, are not able to meet the need for nucleotides by through novo synthesis alone, meaning the preferential route is recovery of nucleotides from diet. In situations where stress affects the immune system (patients in critical situation) dietary supplementation with nucleotide formulations is essential to maintain the humoral and cellular response of the immune system (A. Gil, *European Journal of Clinical Nutrition*, 56 suppl 3, S1-S4 (2002)). It has been specifically shown that exogenous nucleotide supplements stimulate proliferation of lymphoid cells and the lymphoproliferative response to alloantigens and mitogens. This supplementation also contributes to T-lymphocyte response, increases delayed cutaneous hypersensitivity response, increases graft rejection, reverts immunosuppression associated to malnutrition, increases resistance to certain infections, regulates the number of natural killer (NK) cells and macrophages, and promotes the synthesis of immunoglobulin (J. Maldonado et al, *Early Human Development*, 65 Suppl., S69-S74 (2001)).

Supplementation with nucleotides has been studied in randomised clinical studies (RCS) conducted in critical patients. A meta-analysis of 13 studies concluded that supplementation has no effect on mortality, but does significantly reduce the incidence of infections and the duration of hospitalisation (R. J. Beale et al., *Crit. Care Med.*, 27, 799-805 (1999)).

On the other hand, some studies have shown that dietary supplementation with certain polysaccharides from extracts of fungi, yeast or bacteria (especially α-glucans and β-glucans) has a positive effect on the immune response.

β-glucans are a heterogeneous group of glucose polymers that have been studied during recent years because of their biological effects on mammals. It has been described that β-glucans act as activators of the immune system and cellular response modifiers. The binding of β-glucans to their specific intestinal receptors leads to modulation in the expression of cytokines, transcription and growth factors that regulate the immune response. This regulation has demonstrated benefits for palliating immunosuppression and for preventing the haematopoiesis associated to chemotherapy and radiotherapy. Additionally, it has been shown that β-glucans confer certain anticarcinogen activity, preventing oncogenesis and metastatis (D. Akramienė et al., *Medicina (Kaunas)*, 43(8), 597-606 (2007)).

α-glucans are a group of glucose polymers, bound by links α(1-4) and/or α(1-6). An example for obtaining these compounds from an extract of *Lentinus edodes*, a basidiomycete fungus, is described in patent documents EP 733647 (see also U.S. Pat. No. 5,756,318), U.S. Pat. No. 6,831,067 and U.S. Pat. No. 7,169,762. Researches carried out during the last ten years in humans and animals have shown that oral supplementation with these polysaccharides has an immunomodulatory effect. In animal model an increase in TNFα levels has been described, which significantly reduces the size of metastatic tumours in rats. At the same time, they prevent the hepatotoxicity induced by carbon tetrachloride and they protect rats treated with cytosine arabinoside (used in chemotherapy). Studies carried out in humans have demonstrated that oral supplementation with polysaccharides reduces the recurrence of hepatocellular carcinoma and in general, the side effects associated to chemotherapy (E. L. Spierings et al., *J Nutr Sci Vitaminol*, 53, 536-539 (2007)).

There are documents that describe the use of a combination of nucleotides with other nutrients to palliate immunosuppression in critical patients. For example, in patent application EP 367724 (see also U.S. Pat. No. 5,231,085), a combination of nucleotides with arginine and polyunsaturated fatty acids to improve the immune response in humans has been described.

Although nucleotides and extracts rich in polysaccharides from fungi, yeasts and bacteria administered alone can lead to a certain level of immunostimulation or reduction of immunosuppression associated with the critical condition, to date, it has neither been described nor suggested the combination of a nucleobase or a source of nucleobases (for example, nucleotides, nucleosides, RNA or DNA) with a polysaccharide from an extract of fungi, yeast or bacteria. The effect of this combination on the immune response has neither been described.

DISCLOSURE OF THE INVENTION

Unexpectedly, it has now been observed that the combination of a nucleobase or a source of nucleobases with a polysaccharide obtainable from extract of fungi, yeast or bacteria improves the effect on different parameters in comparison to the effects of each separate component. This combination has also proved to have a synergic effect.

Thus, the invention relates to a composition comprising:
a component a) comprising a nucleobase and/or a source of nucleobases; and
a component b) comprising a polysaccharide obtainable from extract of fungi, yeast or bacteria.

In a preferred embodiment of the invention, the composition comprises, in one unit dose:
a component a) comprising from 15 mg to 3,000 mg of a nucleobase and/or a source of nucleobases; and
a component b) comprising from 15 to 3,000 mg of a polysaccharide obtainable from extract of fungi, yeast or bacteria.

Preferably, the compositions are formulated to permit one unit dose that comprises from 30 mg to 2,100 mg, more preferably from 150 mg to 750 mg of a nucleobase and/or a source of nucleobases.

Also preferably, the compositions are formulated so that one unit dose comprises from 30 mg to 2,100 mg, more preferably from 150 mg to 750 mg of a polysaccharide obtainable from extract of fungi, yeast or bacteria.

Also preferably, the compositions are formulated so that one unit dose comprises, between 1 mg and 60 mg per kg of body weight of a mammal, including a human, of the component a) and between 1 mg and 60 mg per kg of body weight of a mammal, including a human, of the component b).

In another embodiment of the invention, the source of nucleobases is selected from the group consisting of nucleosides, nucleotides, RNA and DNA.

In another embodiment of the invention, the polysaccharide is an α-glucan or a β-glucan, preferably the polysaccharide α-glucan is an α-1,4-glucan or an acetylated derivative thereof.

In another embodiment of the invention, the weight ratio between component a) and component b) is between 25:75 and 75:25, more preferably the weight ratio between component a) and component b) is 50:50.

In another embodiment of the invention, the component a) further comprises glutamine.

In a particularly preferred embodiment of the invention, the component a) is Nucleoforce® and the component b) is AHCC®.

In another particularly preferred embodiment of the invention, the component a) is Nucleoforce® Dogs and the component b) is AHCC®.

In a particular embodiment, the composition of the invention is an immunostimulant composition.

In another particular embodiment, the composition of the invention is a pharmaceutical composition.

In another particular embodiment, the composition of the invention is a dietary composition.

The present invention also relates to a process for preparing a composition defined above, which comprises mixing components a) and b) in solid state, preferably, by unit dose, the weight of component a) is between 15 mg and 3,000 mg and the weight of component b) is between 15 mg and 3,000 mg.

In a preferred embodiment, by unit dose, the weight of the component a) is between 1 mg and 60 mg per kg of body weight of a mammal, including a man, and the weight of component b) is between 1 mg and 60 mg of body weight of a mammal, including a human.

The present invention also relates to a composition defined above, for use as a medicament.

The present invention also relates to a composition defined above, for use in the treatment, prevention or prophylaxis in a mammal, including a human, of immunosuppression, of the toxicity derived from chemotherapy or radiotherapy, of a disease of the immune system, cancer, of an infection or for stimulating the immune function.

The present invention also relates to the use of a previously defined composition, for the preparation of a medicament for the treatment, prevention or prophylaxis of immunosuppression in a mammal, including a human.

In a preferred embodiment of the invention, the immunosuppression is associated to cancer, surgery, sepsis, trauma, burns, immunosuppressant treatment, malnutrition or an infection. In another preferred embodiment, the immunosuppression is associated to chemotherapy or radiotherapy treatments.

The present invention also relates to the use of a composition defined above, for the preparation of a medicament for the treatment, prevention or prophylaxis of the toxicity derived from chemotherapy or radiotherapy treatments in a mammal, including a human, preferably the toxicity is selected from the group consisting of haematological, digestive, renal, urinary, cardiac, respiratory, neurological, cutaneous and hepatic toxicity.

The present invention also relates to the use of a composition defined above, for the preparation of a medicament to stimulate the immune function in a mammal, including a human.

The present invention also relates to the use of a composition described above, for the preparation of a medicament for the treatment, prevention or prophylaxis of a disease of the immune system in a mammal, including a human. Preferably, the disease of the immune system is selected between a group consisting of rheumatoid arthritis, lupus erythemathosus, Grave's disease, Reiter's syndrome and Sjögren's syndrome.

The present invention also relates to the use of a composition defined above, for the preparation of a medicament for the treatment, prevention or prophylaxis of cancer in a mammal, including a human.

The present invention also relates to the use of a composition defined above, for the preparation of a medicament for the treatment, prevention or prophylaxis of an infection in a mammal, including a human, preferably the infection being a viral, fungal, bacterial and parasitic infection. More preferably the infection is viral (for example caused by: respiratory syncytial virus, parainfluenza virus type 1, 3 and 4, influenza A and B, adenovirus, coronavirus, avian influenza virus or herpes virus) and/or bacterial (for example caused by: *Streptococcus* beta-hemolityc group A, *Staphylococcus aureus, Mycoplasma pneumoniae, Chlamydia pneumoniae, Haemophilus influenzae, Klebsiella pneumonia, Histophilus somni, Mannheimia haemolytica, Pasteurella multocida* or *Mycoplasma bovis*) affecting the respiratory airways.

The present invention also relates to the use of a composition defined above, for the preparation of a medicament or a dietary composition for the treatment, prevention or prophylaxis of digestive disorders coursing with alterations of the intestinal mucosa (such as digestive disorders derived from antibiotic therapy, long fasting periods, viral, bacterial, fungal or parasitic infections, autoimmune diseases or inflammatory bowel diseases).

In a preferred embodiment, the medicament to be administered comprises from 1 mg to 60 mg per kg of body weight of the mammal, including a human, of component a) and from 1 mg to 60 mg per kg of body weight of the mammal, including a human, of component b) of the composition defined above.

In another preferred embodiment of the invention, the medicament is for administration via the enteral or parenteral route.

The present invention also relates to the use of a composition defined above, in a process for preparing a dietary composition for the stimulation of the immune function of the human body or any other mammal. Preferably the dietary composition comprises from 1 mg to 60 mg per kg of body weight of the mammal, including a human, of component a) and from 1 mg to 60 mg per kg of body weight of the mammal, including a human, of component b) of the composition defined above.

In a preferred embodiment, the mammal is selected from the group consisting of man, dog, cat, horse, cow, pig, piglet, sheep and chicken. Among them, the preferred mammal is the dog.

In the invention, the term "one unit dose" will be understood to be one daily dose or a dose that can be administered more than once daily.

Nucleobases or nucleic bases are cyclical organic compounds that include one or more nitrogen atoms. They are an essential part of nucleosides, nucleotides and nucleic acids. The most preferred nucleobases that form part of the compositions of the present invention are the purine bases (adenine and guadine) and the pyrimidine base (cytosine, thymine and uracil).

The term "source of nucleobases" refers to nucleosides, nucleotides, RNA (ribonucleic acid), DNA (deoxyribonucleic acid) or equivalents.

The component a) of the compositions of the invention comprises free-form nucleobases and/or a source of nucleobases, for example nucleosides, nucleotides, RNA, DNA or mixtures of these.

Nucleosides include ribose nucleosides such as adenosine, guanosine, uridine and cytidine and deoxyribose nucleosides such as deoxyadenosine, deoxyguanosine, deoxyuridine and deoxycytidine.

Nucleotides include phosphate esters of nucleosides, such as monophosphates of adenosine (AMP), guanosine (GMP), uridine (UMP), cytidine (CMP), deoxythymidine (dTMP) and deoxycytidine (dCMP) as well as the di- and tri-phosphates of the nucleosides such as UDP and UTP.

The origin of the source of nucleobases is preferably yeasts, although meat products or similar can also be used.

Therefore, for example, the products Nucleoforce®, Nucleoforce® Dogs and Nucleoforce® Piglets can be obtained from extraction, purification and hydrolysis of the ARN from *Saccharomices cerevisiae*. Depending on the conditions of the process, for example, Nucleoforce®, Nucleoforce® Dogs or Nucleoforce® Piglets, among others, will be obtained. These products are marketed by the company Bioibérica S.A. (www.bioiberica.com). The differences in the composition and profile of nucleotides of component a) of the compositions of the invention respond to differences in the nutritional needs of the species to which the compositions of the invention are destined.

For the purposes of the present invention, the polysaccharides obtained from extracts of fungi, yeasts or bacteria are glucose polymers bound by beta (β(1-3), β(1-4) and/or β(1-6) bonds as well as α(1-4) and/or α(1-6) bonds or any other polysaccharide that contains combinations of the bonds described above. Likewise, the present invention also contemplates derivatives of, for example, methylated or acetylated forms of the aforementioned natural polysaccharides.

Preferably, the polysaccharides of the component b) of the compositions of the invention can be obtained, for example, from Basidiomycete fungi of the following species: *Lentinus edodes, Grifola frondosa, Schizophillum commune, Sclerotinia sclerotiorum, Agaricus bisporus, Pholiota nameko, Pleurotus ostreatus, Flammulina velutipes, Ganoderma lucidum, Auricularia auricular, Ganoderma applanatum, Coriolus versicolor, Grifola umbellata, Volvariella volvácea* and similar, the most preferred being the species *Lentinus edodes.*

The preferred polysaccharide α-1,4-glucan in the present invention comprises units of α-D-glucose joined by (1→4) bonds. This can be represented by the following structure:

where R is a hydrogen atom or an acetyl group in a ratio of 7:3.

This polysaccharide can be extracted and isolated in a culture medium in which a microorganism belonging to the class Basidiomycetes, particulary *Lentinus edodes* is cultivated in a liquid culture media in the presence of a plant tissue extract. The culture is performed according to aeration culture for ordinary medium temperature.

It is described how to obtain this polysaccharide in the patent document EP 733647 (see also U.S. Pat. No. 5,756,318) and marketed by the company Amino Up Chemical Company with the name AHCC® (www.aminoup.co.jp).

The present invention also contemplates a derivative of this polysaccharide described in U.S. Pat. No. 6,831,067 and U.S. Pat. No. 7,169,762, which can be obtained by reacting a culture solution, obtained by culturing a basidiomycete, with a reaction mixture of a rice bran extracts solution and an enzyme.

The amount of the nucleobases and/or sources of nucleobases and the polysaccharide or polysaccharides obtained from extract of fungi, yeasts or bacteria is dependent on the age of the patient, the clinical situation, the treatment of choice, the pathology to be treated and the route of administration. For example, for an adult mammal (for example, a dog), an immunostimulant response can be achieved with a dose of between 25 mg and 60 mg per kg of body weight of mammal of component a) and between 25 mg and 60 mg per kg of body weight of mammal of component b) of the compositions of the present invention.

The pharmaceutical compositions of the invention can be administered to the patient at the required doses. The compositions may be administered by different routes, for example enteral or parenteral.

The pharmaceutical formulations of the invention will generally be in solid, liquid or gel form. The pharmaceutical formulations in solid form, which can be prepared according to the present invention, include powders, micro-granules (pellets), microspheres, nanoparticles, tablets, dispersible granules, capsules, patches and suppositories. The liquid formulations include solutions, suspensions, emulsions, syrups and elixirs containing commonly used inert diluents such as distilled water, ethanol, sorbitol, glycerol or propylene glycol. It is also contemplated formulations in solid form which can be converted, immediately before being used, into formulations in liquid form. These liquid forms include solutions, suspensions and emulsions.

To prepare the dietary and nutritional compositions, the compositions of the invention are formulated with components and/or excipients used in nutrition. The dietary compositions prepared may be, for example, in solid, liquid, emulsion, suspension or gel form. It is also contemplated formulations in solid form which can be converted, before being used, into formulations in liquid form or into suspensions.

The compositions of the invention can be used as treatment or as palliative treatment, for example to restore the immune response of immunodepressed patients, or preventive or prophylactic purposes, for example, to maintain immune function in patients who are to undergo, for example, chemotherapy or radiotherapy, immunosuppressive treatment or similar.

When the compositions of the invention are used for treatment or as palliation, it is recommended to administer the composition of the invention from the time the depression of immune function is detected until the situation is totally restored.

In preventive treatments it is recommended to administer the composition of the invention preferably for a four week period prior to the patient undergoing, for example, an immunodepressant process.

According to the present invention, it has been found that the compositions of the invention have advantages, such as: (i) subsequent to the administration of a composition of the invention, the immune system responds quickly and effectively; (ii) the compositions of the invention are more efficient, in the different parameters measured, than each of the components separately; (iii) there is a synergic effect between the components a) and b) of the compositions of the invention, plus specifically between Nucleoforce® and AHCC® when they are administered together; (iv) the administration of a composition of the invention comprising Nucleoforce® Dogs and AHCC® enables an improvement of the immune response and a reduction in the hepatic lesion in animals undergoing chemotherapy.

DETAILED DESCRIPTION OF THE PREFERRED EMBODIMENTS

The following examples are for illustrative purposes only, and do not represent a limitation of the scope of this invention.

Set out below are two representative examples of tablet formulations.

Example 1

Nucleoforce® Dogs and AHCC® Tablets for Dogs

The tablets are prepared by conventional methods.
Content of Active Ingredients Per Tablet:

| Nucleoforce ® Dogs | 450 mg |
| --- | --- |
| AHCC ® | 450 mg |

Example 2

Nucleoforce® and AHCC® Tablets for Humans

The tablets are prepared by conventional methods.
Content of Active Ingredients Per Tablet:

| Nucleoforce ® | 1,000 mg |
| --- | --- |
| AHCC ® | 1,000 mg |

Set out below are some examples of trials that can be used to determine the activity of the compositions of the present invention.

Example 3

Protection of the Immune and Hepatic Function of Animals Undergoing Chemotherapy Treatment The purpose of the experiment was to study the impact of the administration of a composition of the invention that comprises Nucleoforce® Dogs and AHCC® on the immune function of dogs undergoing chemotherapy treatment.

Materials and Methods

The clinical study design was randomised and double blind. The protocol was approved by the Ethical Committee of Animal Research at the University of Murcia.

A total of 25 adult beagle dogs with an average 15 kg body weight (healthy males and females between 1 and 2 years old) were divided randomly into four groups (C, A, B and A+B) (n=6) and fed during a 30-day period with a standard commercial diet supplemented with:

Control group C: placebo product (crystalline microcellulose).
Group A: Nucleoforce® Dogs (60 mg/kg body weight).
Group B: AHCC® (60 mg/kg body weight).
Group (A+B): a composition of the invention formed by Nucleoforce® Dogs (30 mg/kg body weight) and AHCC® (30 mg/kg body weight).

After 30 days of receiving supplements together with the standard diet, all the dogs received chemotherapy treatment comprising:
a single dose of Lomustin (70 mg/m$^2$ of body surface) orally, and
a single dose of cyclophosphamide (180 mg/m$^2$ of body surface) orally.

After the chemotherapy treatment, the dogs were monitored daily and clinical signs such as their level of attention/activity were recorded. Serial blood samples were taken weekly for nine weeks subsequent to the administration of the chemotherapy drugs.

All the blood samples were subjected to complete haemograms, the biochemical profile was analysed, plasmatic concentrations of non-specific IgA, IgG and IgM immunoglobulins were measured, as was the percentage of sub-type $CD3^+$, $CD4^+$, $CD8^+$ B and T lymphocytes.

The concentrations of immunoglobulin in plasma were analysed, because they constitute an index of the activity of the immune system, and therefore permit the immunosuppression associated to the chemotherapy treatment to be measured. A full biochemical profile was also carried out to characterise the toxicity of the treatment, especially on hepatic function.

The biochemical measurements were carried out using an Olympus AU400 autoanalyser. The concentration of non-specific immunoglobulins was analysed using the ELISA commercial kits (IgA, IgG and IgM; Bethyl, Tex., USA). The lymphocyte phenotype was determined by flow cytometry using an immunofluorescence detection (FACSCalibur, Becton Dickinson) and the data were analysed using the CELL-Quest™ software.

All the data were analysed using a variance analysis (ANOVA) based on the GLM procedure (general linear model) of the SAS statistical software (1996). For all the treatments, the effect of the experimental treatment and the effect of time were studied, as well as the interaction between both parameters. Mean values were compared using the LS-MEANS SAS procedure. A two-tailed P value <0.05 was considered significant.

Results

One week after the chemotherapy treatment, all the dogs presented severe leucopoenia. The same day, severe symptoms of depression and diarrhea were recorded in 50% (3/6) of the dogs in the control group. The percentage of animals affected was slightly lower in the group treated with Nucleoforce® Dogs (33% (2/6)) and in the group treated with AHCC® (33% (2/6)), while in the group treated with the composition of the invention (Nucleoforce® Dogs and AHCC®) none of the animals (0% (%)) presented clinical signs of the disease.

One week after the chemotherapy treatment, the percentage of B lymphocytes was reduced in all the groups. The percentage of change with respect to the baseline value was of −43, −69, −55 and −50% for group C (control), group A (Nucleoforce® Dogs), group B (AHCC®) and group A+B (Nucleoforce® Dogs and AHCC®) respectively. However, the group of dogs receiving the combination of Nucleoforce® Dogs and AHCC® showed a tendency to recover the percentage of B cells with respect to the other groups, because on day 28 the percentage of change in the ratio of B lymphocytes with respect to the baseline value increased to −23% while in the other three groups the values remained constant throughout the experimental period (−51%, −59% and −49% for the control, groups, Nucleoforce® Dogs and AHCC® groups respectively).

Figure 1:
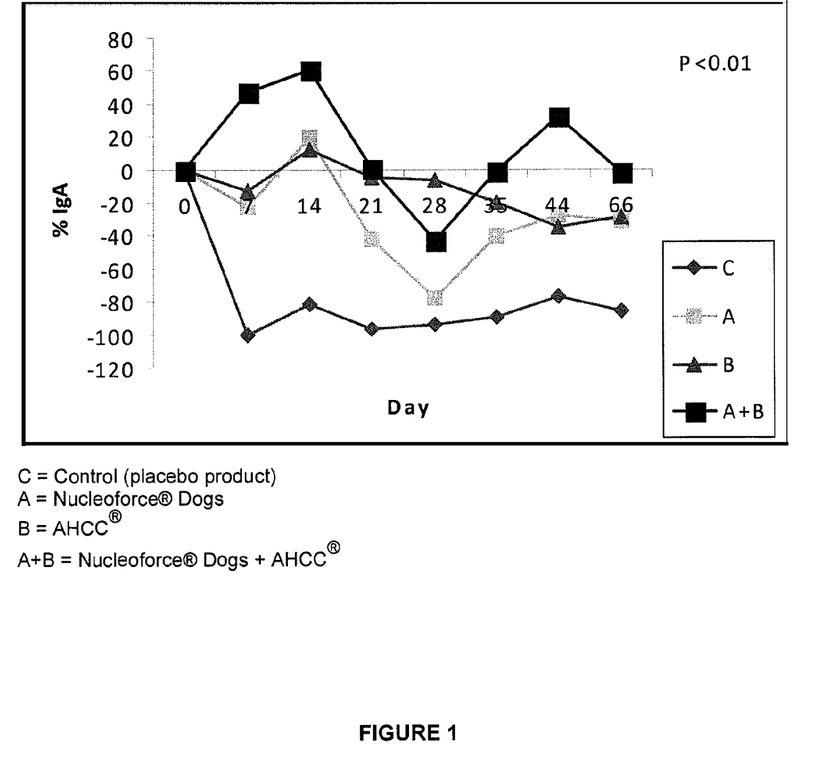
FIG. 1 shows the percentage of variation of the plasma concentration of immunoglobulin A (IgA) with respect to the baseline value of dogs supplemented with the placebo product (C), with Nucleoforce® Dogs (A), with AHCC® (B) and with the composition of the invention comprising the combination of Nucleoforce® Dogs with AHCC® (A+B) after the application of chemotherapy treatment.

The increased recovery of the type B lymphocyte populations was clearly seen in the production of non-specific antibodies. FIG. 1 shows how in Control group C the concentration of IgA fell abruptly seven days after chemotherapy treatment, while in group A (Nucleoforce® Dogs) and in group B (AHCC®) was maintained, and in group A+B (combination of Nucleoforce® Dogs and AHCC®) it increased slightly ($P<0.01$).

Figure 2:
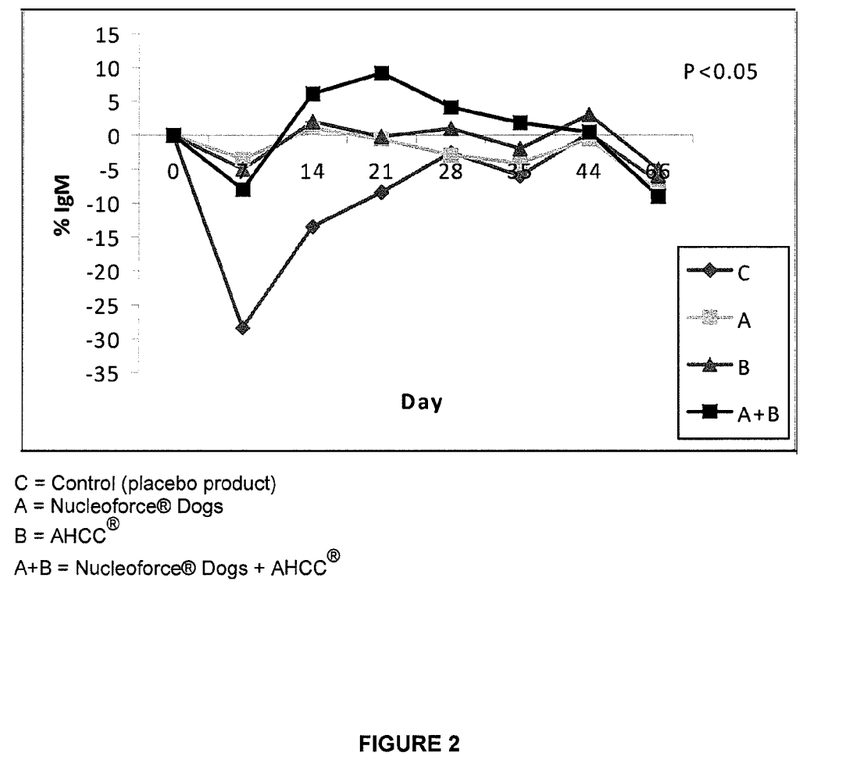
FIG. 2 shows the percentage of variation of the plasma concentration of immunoglobulin M (IgM) with respect to the baseline value of dogs supplemented with the placebo product (C), with Nucleoforce® Dogs (A), with AHCC® (B) and with the composition of the invention comprising the combination of Nucleoforce® Dogs with AHCC® (A+B) after the application of chemotherapy treatment.
Figure 3:
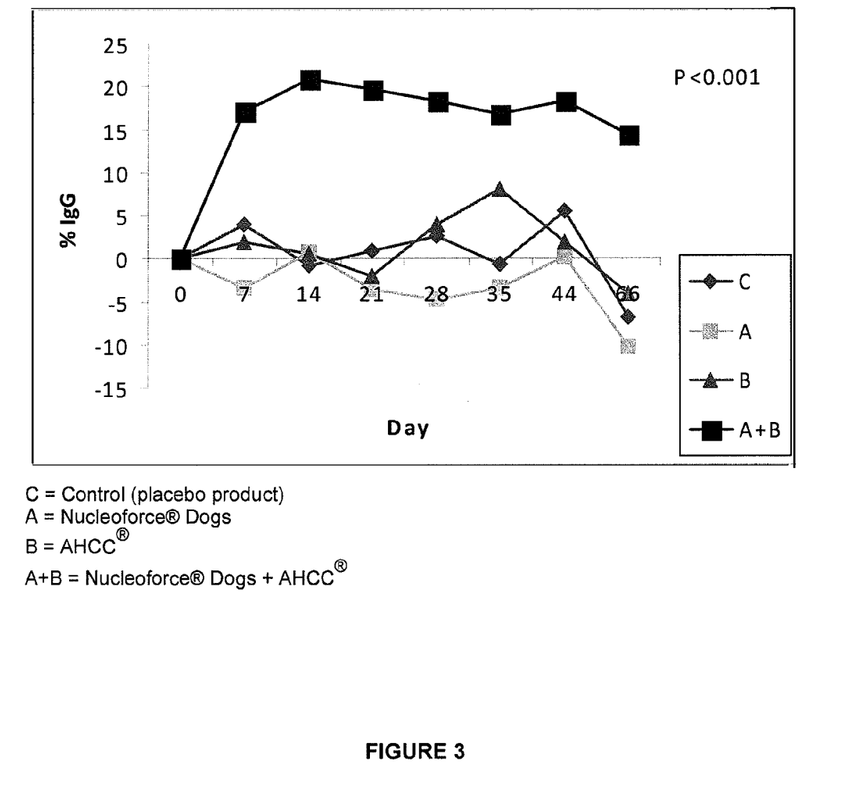
FIG. 3 shows the percentage of variation of the plasma concentration of immunoglobulin G (IgG) with respect to the baseline value of dogs supplemented with the placebo product (C), with Nucleoforce® Dogs (A), with AHCC® (B) and with the composition of the invention comprising the combination of Nucleoforce® Dogs with AHCC® (A+B) after the application of chemotherapy treatment.

The same response pattern is observed in FIG. 2 for the IgM ($P<0.05$). In the case of the IgG (FIG. 3) a significant increase was observed ($P<0.001$) in the plasmatic concentration of immunoglobulin in the group receiving the composition of the invention (combination of Nucleoforce® Dogs and AHCC®) with respect to groups A (Nucleoforce® Dogs), B (AHCC®) and C (control), observing a synergetic effect.

Figure 4:
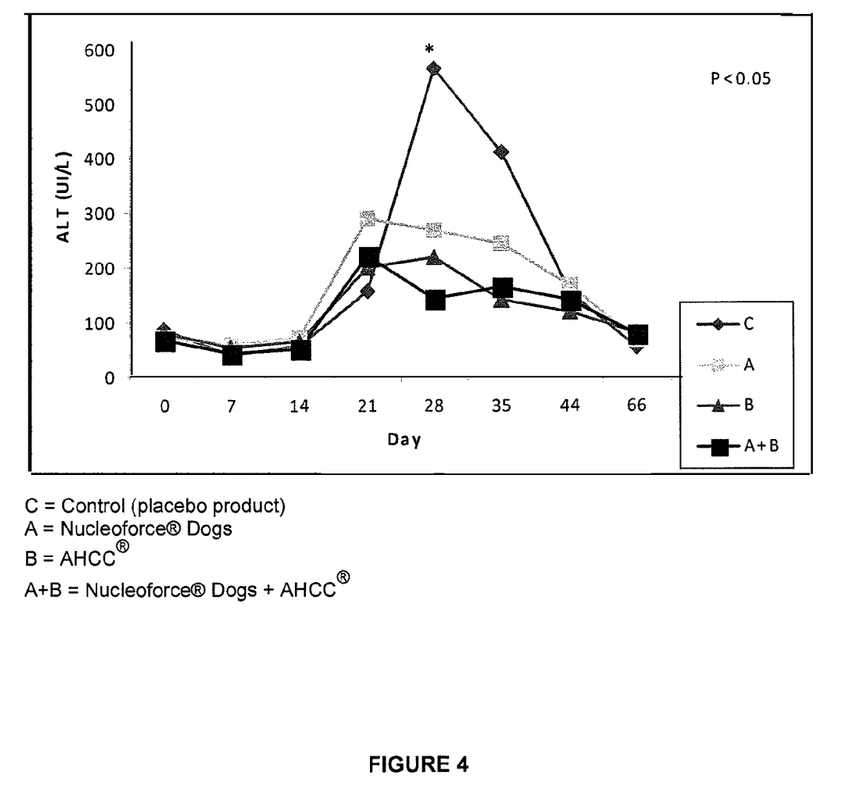
FIG. 4 shows the plasma concentration of the alanine aminotransferase (ALT) of the dogs supplemented with the placebo product (C), with Nucleoforce® Dogs (A), with AHCC® (B) and with the composition of the invention comprising of Nucleoforce® Dogs and AHCC® (A+B) after the application of chemotherapy treatment.

Apart from the effect on the immune function, dietary supplementation with the composition of the invention (Nucleoforce® Dogs and AHCC®) had a protective effect on the hepatotoxicity associated with chemotherapy treatment. As it can be seen in FIG. 4, on day 28 an increase was seen in the serum levels of alanine aminotransferase (ALT) which was significantly higher ($P<0.05$) in the control group (563.8 UI/L) than in groups A (Nucleoforce® Dogs) (266.3 UI/L), B (AHCC®) (221 UI/L) and A+B (Nucleoforce® Dogs and AHCC®) (141.9 UI/L).

The overall results of the study show that the administration of a composition of the invention comprising the combination of Nucleoforce® Dogs with AHCC® enable the immune response to be improved and the hepatic lesions in animals undergoing chemotherapy treatment to be reduced. They also show that there is a synergic effect between Nucleoforce® Dogs and AHCC®, because the effect of the combination surpasses the sum of the individual effects of each component.

Example 4

Reinforcement of the Immune Response in Healthy Animals

The purpose of the experiment was to study the impact of the administration of a composition of the invention that comprises Nucleoforce® Dogs and AHCC® on the immune function of healthy dogs.

Materials and Methods

The study design was randomised and double blind. The protocol was approved by the Ethical Committee of Animal Research at the University of Murcia. A total of 24 adult beagle dogs with an average 15 kg body weight (healthy males and females between 1 and 2 years old) were divided randomly into four groups (C, A, B and A+B) (n=6) and fed during a 30-day period with a standard commercial diet supplemented with:
Control group C: placebo product (crystalline microcellulose).
Group A: Nucleoforce® Dogs (60 mg/kg body weight).
Group B: AHCC® (60 mg/kg body weight).
Group (A+B): a composition of the invention formed by Nucleoforce® Dogs (30 mg/kg body weight) and AHCC® (30 mg/kg body weight).

The animals were monitored daily, and any clinical signs of disease were monitored. In the beginning (day 0) and at the end of the experimental period (day 30) blood samples were taken to determine the index of lymphocyte proliferation in vitro. This index was used because it is considered that it is a measurement that reliably measures the capacity of the immune system to respond to an infection.

To determine the proliferation of lymphocytes, the lymphocytes were isolated in heparinised blood samples from the animals and cultured in absence or presence of phytohaemaglutinin with presence of 10 μm bromodeoxyuridine (5-bromo-2-deoxyuridine, BrdU). The cell proliferation index was determined using a non-radioactive ELISA technique (Cell proliferation ELISA; Boehringer Mannheim, Germany). The results were expressed as optical density units (OD).

All the data were analysed using a variance analysis (ANOVA) based on the GLM procedure (General Linear Model) of the SAS statistical software (1996). Mean values were compared using the LS-MEANS SAS procedure. A two-tailed P value <0.05 was considered significant.

Results

Figure 5:
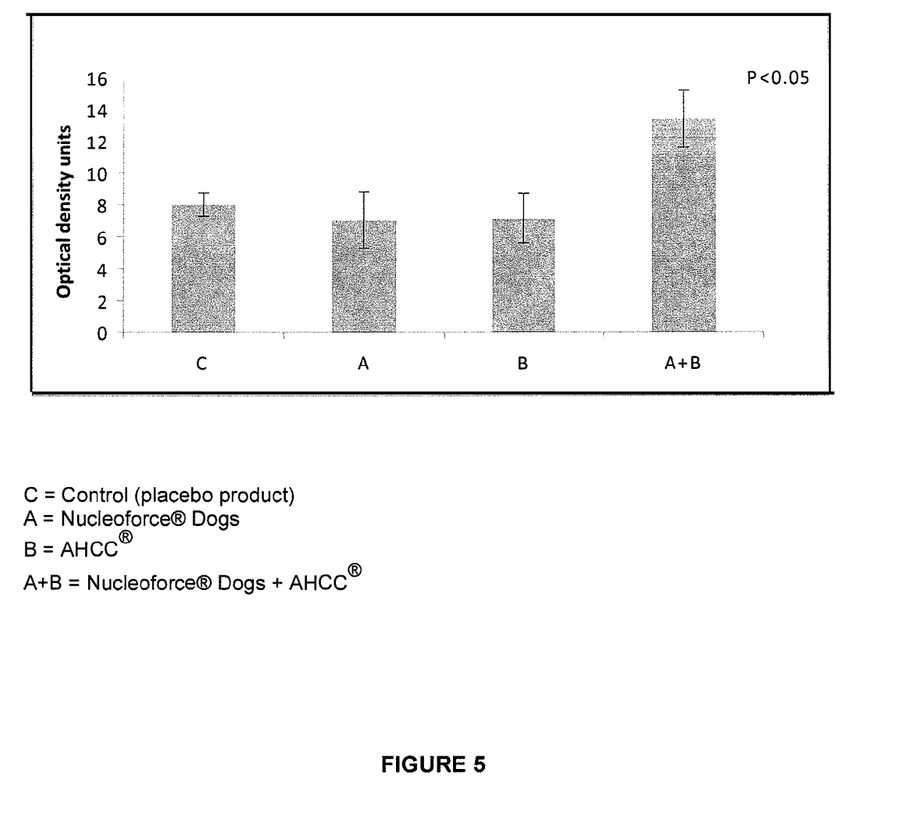
FIG. 5 shows the index of lymphocyte proliferation of healthy dogs supplemented with the placebo product (C), with Nucleoforce® Dogs (A), with AHCC® (B) and with the composition of the invention comprising of Nucleoforce® Dogs and AHCC® (A+B) over a 30-day period.

As shown in FIG. 5, after 30 days of administering the products to be tested, the animals that received the composition of the invention (combination of Nucleoforce® Dogs and AHCC®) presented a significantly higher index of lymphocyte proliferation (13.42±0.72 OD) (P<0.05) than that in animals receiving Nucleoforce® Dogs (7.04±1.72 OD), AHCC® (7.18±1.79 OD) or placebo product (8.01±1.81 OD).

No signs of toxicity were observed associated to the administration of the product.

These results showed the preventive or prophylactic effect of the composition of the invention that comprises the combination of Nucleoforce® Dogs and AHCC®, given that the administration of this composition improves the immune response capacity, enabling the animal to be prepared for any processes capable of causing depression of the immune system.

Example 5

Effects of Supplementing a Combination of Nucleoforce® and AHCC® to Dairy Calves Prior Weaning on Respiratory Afflictions and Immune Response During the Postwening Period The aim of the present study was to test the effect of a combination of Nucleoforce® and AHCC® on the incidence of respiratory problems and immune function of weaning calves from a commercial farm with a high incidence of respiratory disease.

Materials and Methods 78 dairy replacement calves (initial age=18±6.3 days and body weight=43±6.1 kg) were fed with 2 L of milk replacer (MR) twice daily via a bottle at 07.30 h and 16.30 h until 45 days of life, and then a daily dose of 2 L of MR at 07.30 h for an additional week. At 37 day of age half of the calves received a daily dose of 3 g of the combination of Nucleoforce® (Bioiberica, Spain) and AHCC (AminoUp, Japan) supplemented through the morning feeding of MR until weaning time (52 days). After weaning, calves were moved from individual hutches into pens holding 8 animals until reaching 111±2.1 days (when the study was completed). Animal performance was monitored from 52 until 111 days of life. Respiratory afflictions were monitored daily from 37 to 111 days of life. Blood samples from half of the animals randomly chosen from each treatment group were obtained by venipuncture of the jugular vein at the age of 37 days and 52 days. Incidence of respiratory afflictions was analyzed using mixed-effects logistic regression analysis, and the number of respiratory cases using a mixed-effects Poisson regression analysis. Blood determinations were analysed using a mixed-effects ANOVA.

Results

Blood plateletcrit was higher (P<0.05) in supplemented than in control calves (22.9 vs 21.5±0.45%, respectively). Also, means platelet volume was higher (P<0.05) in supplemented than in control calves (10.3 vs 7.9±0.01 fL, respectively). Similarly, the percentage of monocytes was also higher (P<0.05) in supplemented than in control calves (10.7 vs 9.1±0.10%, respectively).

Figure 6:
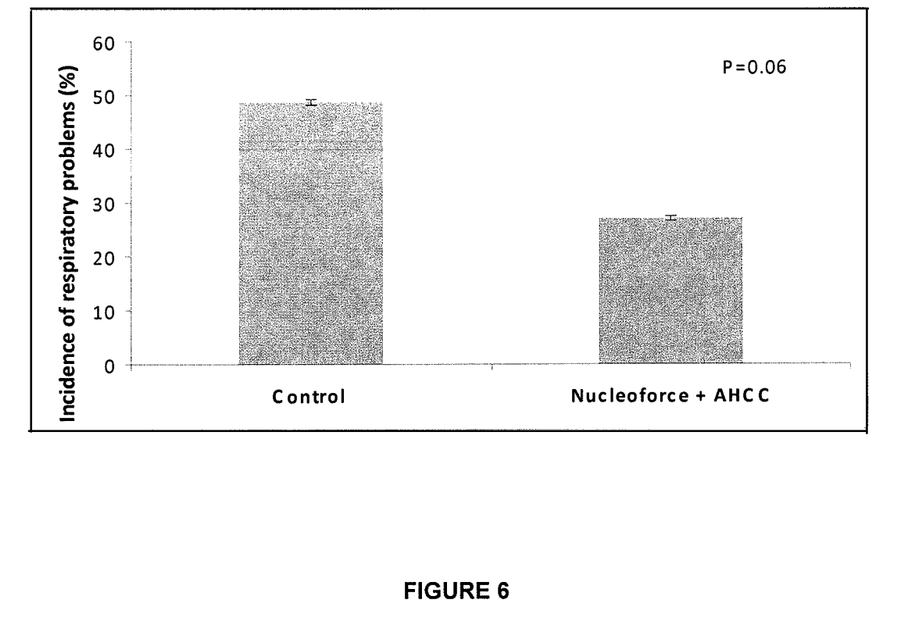
FIG. 6 shows the incidence of respiratory problems (%) from day 37 until day 111 of life in dairy calves receiving a milk replacer supplemented either with the placebo product (Control) or with the composition of the invention comprising of Nucleoforce® and AHCC® (A+B) from day 37 until day 52 of life.

As can be seen in FIG. 6, the incidence of animals affected by respiratory problems tended (P=0.06) to be lower in calves that received the supplement (27±0.45%) than in the unsupplemented animals (48.7±0.51%).

It could be concluded that 3 g/day of the combination of Nucleoforce® and AHCC tended to be effective in providing animals with an adequate immune response to reduce the incidence of respiratory upsets during transition from liquid to solid feeds.

The invention claimed is:

1. A composition consisting essentially of the following components:
   a) nucleotides, wherein the nucleotides are extracted from hydrolyzed yeast; and
   b) an α-1,4-glucan obtainable from an extract of *Lentinus edodes*.

2. The composition according to claim 1, wherein the component a) is present in an amount from 15 mg to 3,000 mg of the nucleotides; and the component b) is present in an amount from 15 mg to 3,000 mg of the α-1,4-glucan.

3. The composition according to claim 1, wherein the component a) is present in an amount between 1 mg and 60 mg per kg of body weight of a mammal, and the component b) is present in an amount between 1 mg and 60 mg per kg of body weight of a mammal.

4. The composition according to claim 1, wherein the component a) and the component b) are present at a weight ratio between 25:75 and 75:25 of the component a) to the component b).

5. The composition according to claim 4, wherein the weight ratio of the component a) and the component b) is 50:50.

6. A composition consisting essentially of the following components:
   a) nucleotides, wherein the nucleotides are extracted from hydrolyzed yeast;
   b) an α-1,4-glucan obtainable from an extract of *Lentinus edodes*; and glutamine.

7. An immunostimulant composition consisting essentially of the composition according to claim 1, in an amount effective to stimulate proliferation of lymphocytes.

8. A process for preparing the composition according to claim 1, comprising mixing components a) and b) in solid state.

9. A method of stimulating lymphocyte proliferation in a mammal in need thereof, comprising administering to the mammal the composition of claim 1 in an amount effective to stimulate lymphocyte proliferation.

10. The method according to claim 9, wherein the mammal is a human or dog.

* * * * *